United States Patent [19]

Shen

[11] 4,135,884
[45] Jan. 23, 1979

[54] GAMMA STICK

[76] Inventor: James T. Shen, 940 Cornell Rd., Pasadena, Calif. 91106

[21] Appl. No.: 828,542

[22] Filed: Aug. 29, 1977

[51] Int. Cl.² ............................................ G01N 33/16
[52] U.S. Cl. ...................................... 422/59; 23/230 B; 424/1; 424/12; 424/16; 195/127; 422/58; 422/102
[58] Field of Search ................ 23/230 B, 253TP, 259, 23/292; 424/12, 16, 1; 195/127

[56] References Cited

U.S. PATENT DOCUMENTS

| 3,770,380 | 11/1973 | Smith | 23/230 B |
| 3,770,383 | 11/1973 | Price | 23/253 TP |
| 3,826,619 | 7/1974 | Bratu et al. | 23/253 TP |
| 3,868,219 | 2/1975 | Hurenkamp | 424/12 |

Primary Examiner—R.E. Serwin
Attorney, Agent, or Firm—William W. Haefliger

[57] ABSTRACT

A test stick, usable in clinical assays, is adapted to be inserted in a test tube that contains antigen solution. The stick comprises:
(a) an elongated plastic member having a test portion adapted to be inserted into said solution in the test tube,
(b) said test portion defining surface area at least about as great as the test tube bore surface extending about said test portion,
(c) said test portion adapted to be coated with antibody to contact said solution.

1 Claim, 9 Drawing Figures

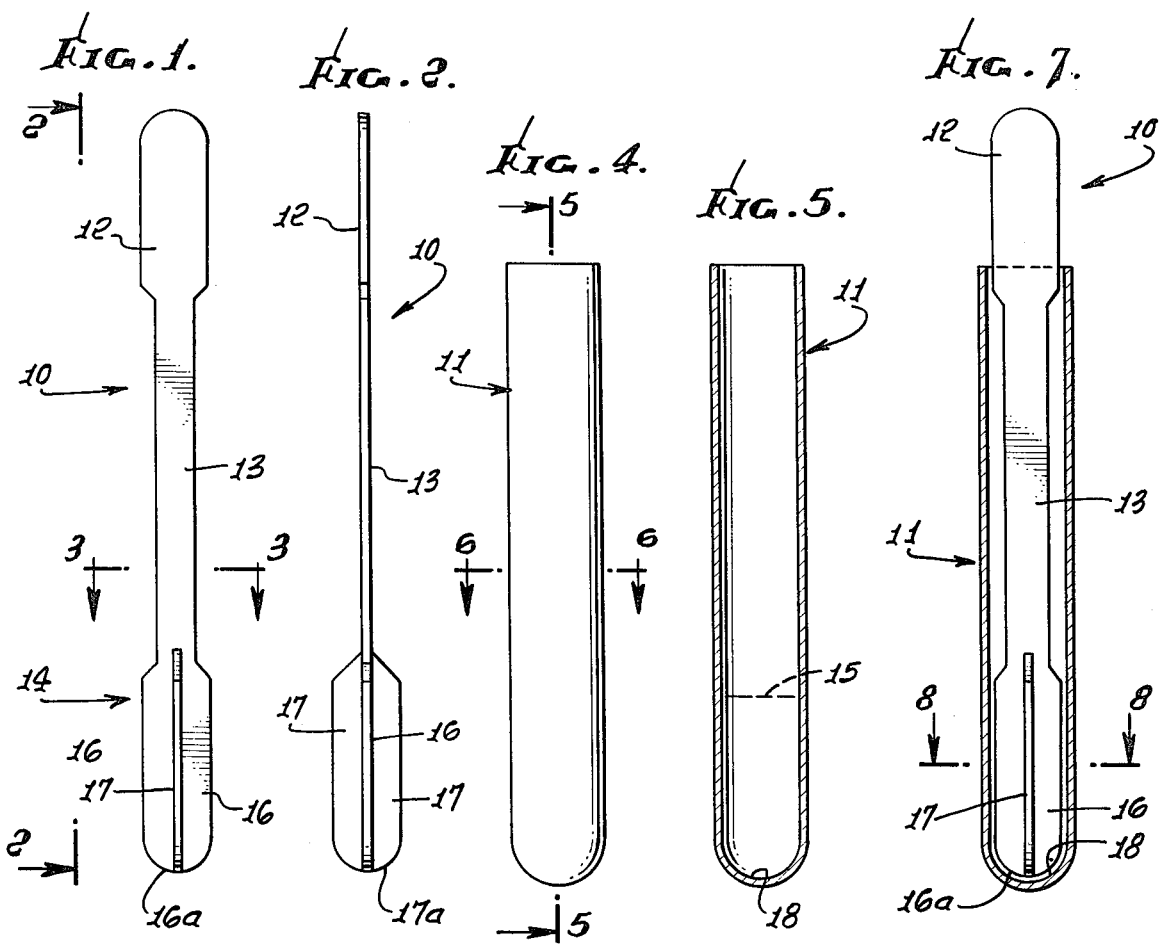
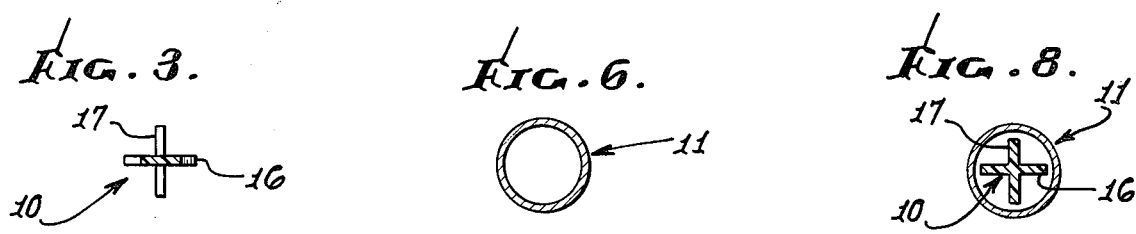
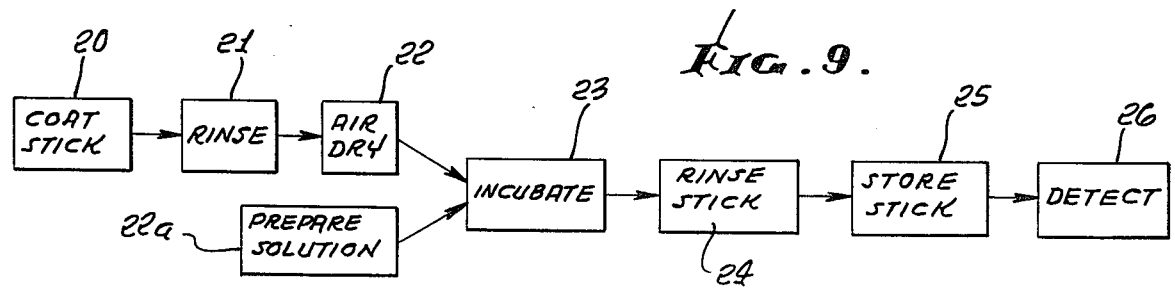

GAMMA STICK

BACKGROUND OF THE INVENTION

This invention relates generally to clinical assay equipment and techniques, and more particularly concerns a test stick to carry a coating of antibody to be inserted in a solution of antigen in a test tube.

Prior clinical or radio immunoassay techniques are exemplified by those described in U.S. Pat Nos. 3,646,346 and 3,867,517. Typically, antibody was coated on a test tube bore; antigen solution was introduced into the tube for incubation contact with the coating, and the solution was thereafter aspirated or decanted from the tube. This technique suffered certain disadvantages, including the need for decounting of the solution and rinse water from the tubes necessitating time consuming and expensive manual labor, particularly when many tubes must be handled.

SUMMARY OF THE INVENTION

It is a major object of the invention to provide a test stick coatable with antibody, and that is easily handled and used in conjunction with a test tube containiing a solution of antigen, whereby the above described problems and disadvantages are obviated. As will be seen, the stick comprises:

(a) an elongated plastic member having a test portion adapted to be inserted into the solution in the test tube,
(b) the test portion defining surface area at least about as great as the tube bore surface extending about the test portion,
(c) said test portion adapted to be coated with antibody to contact the solution.

As will be seen, the test portion may advantageously define multiple flutes, as for example four flutes, providing coating area at least about as great as that of the bore of a test tube into which the flutes are inserted to closely fit that bore; and the stick may consist of molded plastic such as polypropylene for best binding of antibody, for example. The method of employment of the stick typically involves the steps:

(a) coating a test portion of the stick with antibody,
(b) inserting the test portion of the stick into the test tube to immerse the coating in said solution, thereby to effect antibody-antigen reaction, and
(c) removing the stick from the solution, after said reaction is completed, whereby the extent of said reaction may be assayed.

Typically, the antigen is labeled with tracer, as for example radioactive tracer and in the manner as described in U.S. Pat. No. 3,646,346; and the extent of bonding is determined by detection of the tracer.

These and other objects and advantages of the invention, as well as details of an illustrative embodiment, will be more fully understood from the following drawings, and description, in which:

DRAWING DESCRIPTION

FIG. 1 is a side elevation of a stick embodying the invention;

FIG. 2 is a side elevation on lines 2—2 of FIG. 1, of the stick;

FIG. 3 is a horizontal section on lines 3—3 of FIG. 1;

FIG. 4 is a side elevation of a tube to be used with the FIG. 1 stick;

FIG. 5 is a vertical section on lines 5—5 of FIG. 4;

FIG. 6 is a horizontal section on lines 6—6 of FIG. 4;

FIG. 7 is a vertical section showing the FIG. 1 stick on the FIG. 4 tube;

FIG. 8 is a horizontal section on lines 8—8 of FIG. 7; and

FIG. 9 is a flow diagram.

DETAILED DESCRIPTION

The test stick 10 shown in FIGS. 1-3 is adapted to be inserted in the tube 11 of FIGS. 4-6, as for example in the manner and to the extent as seen in FIGS. 7 and 8, for incubation purposes.

The FIG. 1 stick comprises an elongated plastic member having upper, medial and lower portions 12-14. Upper flat portion 12 is wider than the middle flat stem portion 13, to provide a handle, its width being slightly less than the bore diameter of tube 11, to fit nicely therein. The lower test portion of the stick is adapted to be inserted into the antigen solution in the lower portion of the tube, at a level such as indicated at 15 in FIG. 5, whereby the surface of the antibody coating on the lower portion 14 is submerged in the solution. The surface area of the lower portion 14 is at least about as great as the tube bore surface area extending about the test portion, i.e. below level 15, whereby coating that bore with the substance on the stick may be eliminated, while the benefits of the function of such bore coating are retained and enhanced.

More specifically, the test portion 14 typically defines multiple flutes, as for example four longitudinal flutes. These include like and opposite flutes 16 in the plane of stick portions 12 and 13, and like and opposite flutes 17 normal to that plane. They project laterally to fit closely but nicely within the tube bore, and their lower ends are typically curved or rounded as at 16a and 17a to fit the concave inner surface 18 of the tube bottom wall. At such time, the upper handle portion 12 projects from the tube. The entire stick typically consists of plastic such as molded polypropylene.

Typical steps employed in using the stick are described as follows, with reference to FIG. 9. The stick lower end portion 14 is first coated with antibody, as indicated at 20. One example of this would be to submerge the stick portion 14 in aqueous antibody solution in Tris buffer solution, pH 9 to 10, at 0.05 to 0.1 molar concentration. Merely as illustrative, any antibody against steroid such as steroid hormone may be used, examples being T-3, T-4 and TSH (thyroid stimulating hormone). See also U.S. Pat. No. 3,867,517, for coating techniques.

After 30 minutes submergence, the stick is withdrawn, rinsed twice in distilled water as indicated at 21, and air dried at room temperature. See box 22 in FIG. 9.

For test purposes, an aqueous solution is prepared containing 1 mil of barbital, buffered to 0.05 molar, pH 8.6. A specific antigen is then added, as for example 100 lamda testing sample, iodinated, i.e. labeled, with tracer iodine 125. See box 22a in FIG. 9. The solution is prepared in, or transferred into, tube 11. Other tracers are fluorescein isothiocynate, Rhodamine and enzyme.

Next, the coated stick 10 is inserted into the tube, as in FIG. 7, and left in place for an incubation period of 30-60 minutes, at room temperature. Bonding of antigen-antibody takes place at this time. See box 23 in FIG. 9. Thereafter, the stick is withdrawn, and rinsed twice in distilled water, as indicated by box 24.

Finally, the stick is inserted in another clean tube 11, for counting, as indicated at 25. Subsequently, the radioactivity associated with stick may be detected at 26, with the stick inserted in a counter. Alternately, the tube containing the antigen or antibody solution from which the stick was removed can be subjected to radioactivity detection or counting, as for example before and after stick insertion and removal, to determine reduction in radioactivity.

It will be noted that the provision of flutes on the stick enables the provision of antibody or antigen coating area at least about as great as, and preferably greater than, the available coating area on the bore of the tube, as in the prior art, whereby greater assay sensitivity is achievable.

The handle may also be used for identification of the stick on which a specific antibody is coated, i.e. the identification may be printed or engraved on the handle portion.

I claim:

1. For use in clinical assays, the combination comprising a test tube and a test stick inserted in the test tube that contains antigen solution, the tube having an upwardly concave bottom wall the stick comprising (a) an elongated plastic member having a test portion inserted into said solution in the test tube,
   (b) said test portion defining surface area at least about as great as the test tube bore surface extending about said test portion,
   (c) said test portion coated with antibody to contact said solution,
   (d) said test portion defining multiple flutes arranged in opposed pairs, each such pair having lowermost edges which are downwardly generally convex in matching relation to the upward concavity of said tube bottom wall,
   (e) the uppermost extent of the stick projecting upwardly from the uppermost top level of the tube when said flute lowermost edges are adjacent the tube bottom wall,
   (f) said member having opposed parallel faces and being flat above the level of the flutes, two of said flutes having opposite surfaces in the same planes as are defined by said opposed parallel faces,
   (g) said stick being narrowed in width between said uppermost extent and said flutes.

* * * * *